US008753998B2

(12) United States Patent
Chiang et al.

(10) Patent No.: US 8,753,998 B2
(45) Date of Patent: Jun. 17, 2014

(54) METHOD FOR PREPARING TITANIUM-SILICALITE MOLECULAR SIEVE AND METHOD FOR PREPARING CYCLOHEXANONE OXIME USING THE MOLECULAR SIEVE

(75) Inventors: Chien-Chang Chiang, Taipei (TW); Cheng-Fa Hsieh, Taipei (TW); Pin-To Yao, Taipei (TW); Shih-Yao Chao, Taipei (TW)

(73) Assignee: China Petrochemical Development Corporation, Taipei (Taiwan), Taipei (TW)

( * ) Notice: Subject to any disclaimer, the term of this patent is extended or adjusted under 35 U.S.C. 154(b) by 133 days.

(21) Appl. No.: 13/344,995

(22) Filed: Jan. 6, 2012

(65) Prior Publication Data

US 2012/0271066 A1      Oct. 25, 2012

(30) Foreign Application Priority Data

Apr. 19, 2011   (TW) .............................. 100113503 A

(51) Int. Cl.
*B01J 21/06* (2006.01)
*C07C 249/04* (2006.01)

(52) U.S. Cl.
USPC ........... 502/242; 564/267; 502/158; 502/172; 502/200; 502/232

(58) Field of Classification Search
USPC .................... 502/158, 172, 200, 232, 242
See application file for complete search history.

(56) References Cited

U.S. PATENT DOCUMENTS

| | | | |
|---|---|---|---|
| 2,071,071 A | 2/1937 | Illingworth | |
| 4,399,247 A * | 8/1983 | Ona et al. ...................... | 524/204 |
| 4,410,501 A | 10/1983 | Taramasso et al. | |
| 5,885,546 A | 3/1999 | Kumar et al. | |
| 6,991,678 B2 | 1/2006 | Dongare et al. | |
| 2004/0152583 A1 * | 8/2004 | Grosch et al. ................... | 502/38 |

FOREIGN PATENT DOCUMENTS

| | | |
|---|---|---|
| EP | 1452637 A1 * | 9/2004 |
| WO | WO 2011032837 A1 * | 3/2011 |

OTHER PUBLICATIONS

Wang et al., "Preparation of titanium silicalite-1 catalytic films and application as catalytic membrane reactors", Chemical Engineering Journal, vol. 156, pp. 562-570 (2010).
Li et al., "The synthesis and characterization of titanium silicalite-1", Journal of Materials Science, vol. 37, pp. 1959-1965 (2002).
Gamba et al., "TS-1 from First Principles", J. Phys. Chem. A, vol. 113, pp. 15006-15015 (2009).
Zhang et al., "Hydrothermal Synthesis of Titanium Silicalite-1 Structurally Directed by Hexamethyleneimine", Ind. Eng. Chem. Res., vol. 48, pp. 4334-4339 (2009).

* cited by examiner

*Primary Examiner* — Samantha Shterengarts
*Assistant Examiner* — Amanda L Aguirre
(74) *Attorney, Agent, or Firm* — Edwards Wildman Palmer LLP; Peter F. Corless; Mark D. Russett

(57) ABSTRACT

The present invention provides a method for preparing a titanium-silicalite molecular sieve, and a method for preparing cyclohexanone oxime using the titanium-silicalite molecular sieve. The method for preparing a titanium-silicalite molecular sieve includes the steps of preparing a mixture of a titanium source, a silicon source and a template agent, wherein the titanium source has a structure of formula (I);

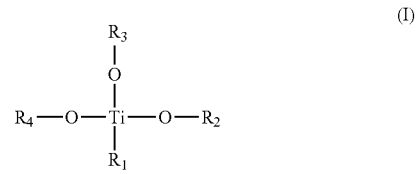

heating the mixture to form a gel mixture; mixing the gel mixture with water; heating the gel mixture mixed with the water in a water bath; and calcining the gel mixture mixed with the water. The method using the titanium-silicalite molecular sieve for preparing cyclohexanone oxime results in high conversion rate and high selectivity.

20 Claims, No Drawings

METHOD FOR PREPARING TITANIUM-SILICALITE MOLECULAR SIEVE AND METHOD FOR PREPARING CYCLOHEXANONE OXIME USING THE MOLECULAR SIEVE

CROSS-REFERENCES TO RELATED APPLICATIONS

This application claims under 35 U.S.C. §119(a) the benefit of Taiwanese Application No. 100113503, filed Apr. 19, 2011, the entire contents of which is incorporated herein by reference.

BACKGROUND OF THE INVENTION

1. Field of the Invention

The present invention relates to a method for preparing a titanium-silicalite molecular sieve, and more particular to, a method for preparing a titanium-silicalite molecular sieve with high reactivity and a method for preparing a cyclohexanone oxime using the titanium-silicalite molecular sieve.

2. Description of the Prior Art

Crystalline titanium-silicalite molecular sieves are formed by incorporating titanium into the zeolite structure of silicon dioxide, and have the MFI structures, which are also named as the TS-1 molecular sieves. U.S. Pat. No. 4,410,501 discloses the preparation of this molecular sieve. Such molecular sieve is used as a catalyst in an oxidation reaction, wherein hydrogen peroxide is used as an oxidant. However, the hydrolysis rate of the titanium source is too fast to match the hydrolysis rate of the silicon source, such that the two materials may not be mixed evenly, and the order degree of the material is decreased. Moreover, the titanium source may become anatase, and the catalyst is thus degraded. Therefore, it is important to have even mixing of materials and proper hydrolysis rates of the titanium source and the silicon source, and to avoid the formation of anatase.

Chemical Engineering Journal 156 (2010) 562-570, Journal of Materials Science 37 (2002) 1959-1965, J. Phys. Chem. A 2009, 113, 15006-15015, Ind. Eng. Chem. Res. 48, 4334-4339, 2009 disclose UV-visible diffuse reflectance spectra of TS-1, wherein the peak at 220 nm represents the bonding of titanium-oxygen-silicon, and the peak at 330 nm represents the bonding of titanium-oxygen-titanium. The higher titanium content results in more significant peak at 330 nm. The MFI structure is based on the bonding of titanium-oxygen-silicon, and thus the conventional technology focused on the reduction of the bonding of titanium-oxygen-titanium, and developed the methods for lowering the titanium content. However, the lower titanium content results in fewer activity spots on the TS-1 molecular sieve and lower catalyst activity.

UK Patent GB 2071071 discloses using TEOT (titanium tetraethoxide) as the titanium source for preparing TS-1 catalysts; however, the hydrolysis rate of the TEOT is faster than that of the silicon source, TEOS (silicon tetraethoxide), such that the bonding of titanium-oxygen-titanium is formed, and the titanium content in the molecular sieve structure is reduced. U.S. Pat. No. 4,410,501 discloses that the TEOT is oxidized by hydrogen peroxide into the titanium peroxide solution, which avoids the formation of titanium-oxygen-titanium bonding, before the preparation of TS-1 catalysts. However, U.S. Pat. No. 6,991,678B2 discloses that the titanium peroxide solution is unstable in the basic environment, such as interaction with the neutral or basic template agent.

U.S. Pat. No. 5,885,546 discloses using acetylacetone for preparing TS-1 catalysts to decrease the hydrolysis rate of the titanium source. Accordingly, it is important to have close hydrolysis rates of the titanium source and the silicon source for preparing TS-1 catalysts with a proper titanium-oxygen-silicon structure.

Hence, it is an urgent issue to develop a method for preparing a titanium-silicalite molecular sieve with a high activity so as to improve the usage efficiency of hydrogen peroxide and favor the application in the industry.

SUMMARY OF THE INVENTION

The present invention provides a method for preparing a titanium-silicalite molecular sieve. The method includes the steps of preparing a mixture of a titanium source, a silicon source and a template agent, wherein the titanium source has a structure of formula (I)

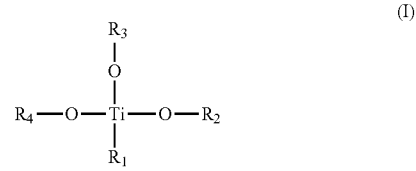

wherein $R_1$, $R_2$, $R_3$ and $R_4$ are independently $C_1$-$C_{10}$alkyl, $C_1$-$C_{10}$alkoxy, $C_2$-$C_{10}$hydroxyalkyl,

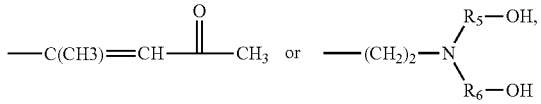

in which $R_5$ and $R_6$ are independently $C_1$-$C_3$alkyl, and at least two of $R_1$, $R_2$, $R_3$ and $R_4$ have a carbon number more than 4; heating the mixture to form a gel mixture; mixing the gel mixture with water; heating the gel mixture mixed with the water in a water bath; and calcining the gel mixture mixed with the water.

The present invention further provides a method for preparing cyclohexanone oxime. The method includes the step of performing a reaction of cyclohexanone, ammonia and hydrogen peroxide in the presence of a titanium-silicalite molecular sieve of the present invention and a solvent.

Specifically, in the present invention, the silicon source and the titanium source are mixed at the low temperature and under nitrogen sealing, added with a template agent solution (alcohol solution or aqueous solution), and added with water drop by drop. After removing the alcohol and adding the water, the gel mixture mixed with the water is sealed in a stainless steel can to be heated in a water bath. Then, the solid is separated from the liquid, and the gel mixture is calcined.

In one embodiment, $R_1$ is $C_6$-$C_{10}$alkoxy, and $R_2$, $R_3$ and $R_4$ are independently $C_6$-$C_{10}$alkyl. In one embodiment, $R_1$ is $C_6$-$C_{10}$alkyl, and $R_2$ and $R_3$ are independently $C_2$-$C_{10}$hydroxyalkyl, and $R_4$ is $C_6$-$C_{10}$alkyl.

In one embodiment, $R_1$ is $C_1$-$C_4$alkoxy, $R_2$ and $R_3$ are independently

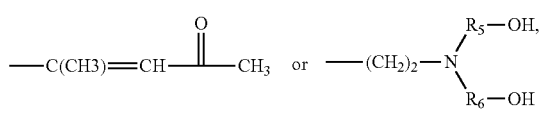

and R$_4$ is C$_1$-C$_4$alkyl.

For example, R$_1$ is C$_1$-C$_4$alkoxy, R$_2$ and R$_3$ are

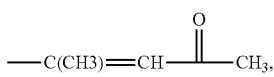

and R$_4$ is C$_1$-C$_4$alkyl. Alternatively, R$_1$ is C$_1$-C$_3$alkoxy, R$_2$ and R$_3$ are

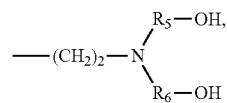

and R$_4$ is C$_1$-C$_3$alkyl.

In the present invention, the titanium source may be titanium ethylhexoxide, titanium di(2-ethylhexoxy)bis(2-ethyl-1,3-hexanediolate, titanium di-isopropoxide bis(acetylacetonate, titanium bis(tri-ethanolamine)di-isopropoxide or a combination thereof.

In the present invention, the silicon source is tetraalkyl silicate, polyethoxysiloxane or a mixture thereof. The silicate may be tetraalkyl silicate such as tetramethyl silicate, tetraethyl silicate, tetrapropyl silicate or tetrabutyl silicate. The polyethoxysiloxane may be ES-28 (n=1~2), ES-32 (n=3~4) or ES-40 (n=4~5) (Colcoat CO.)

Further, the molar ratio of the titanium source to the silicon source ranges from 0.005:1 to 0.06:1; and the molar ratio of the template agent to the silicon source ranges from 0.1:1 to 0.5:1.

In the present invention, the template agent includes tetrapropylammonium hydroxide in a solvent comprising at least one alcohol or an aqueous solution. For example, the tetrapropylammonium hydroxide is dissolved in an alcohol or water for the anion exchange resin process. The alcohol is a linear or branched alcohol having 1 to 8 carbons such as methanol, ethanol, isopropanol, n-butanol or tert-butanol. The alcohol concentration of the template agent solution may be 5 wt % to 50 wt %.

In the method of the present invention, the gel mixture mixed with the water is heated to remove the solvent. The water includes silicon dioxide, and the silicon dioxide is 0.1 to 50 wt % of the water. The weight ratio of the water to the gel mixture is in a range from 0.001:1 to 0.5:1.

In the present invention, the water including silicon dioxide may be silicon dioxide gel solution (or colloidal silica) such as Ludox AS-40, Ludox AS-30, Ludox TM-40, Ludox TM-50, Ludox AM-30, Ludox HS-30, Ludox HS-40 (DuPont) or SNOWTEX-40, SNOWTEX-50, SNOWTEX-C, SNOWTEX-N, SNOWTEX-20L, SNOWTEX-ZL, SNOW-TEX-UP (Nissan Chemical Industries, Ltd.)

In the method for preparing cyclohexanone oxime, the reaction is performed at 1 atm or higher pressure, and 40 to 110° C., preferably 50 to 90° C. In the reaction, the amount of the titanium-silicalite molecular sieve is 0.1 to 10 wt % of the total amount of reactants. Preferably, the amount of the titanium-silicalite molecular sieve is 1 to 5 wt % of the total amount of reactants. The molar ratio of ammonia to cyclohexanone ranges from 1.2:1 to 2:1, preferably 1.4:1 to 1.8:1; and the molar ratio of hydrogen peroxide to cyclohexanone ranges from 0.7:1 to 2.0:1, preferably 1.0:1 to 1.5:1. The concentration of hydrogen peroxide is 30 wt % to 50 wt %. The hydrogen peroxide is gradually added in the reaction. The preparation of cyclohexanone oxime may be performed in the presence of a solvent such as a polar solvent, which may be one or more selected from the group consisting of an alcohol, a ketone and water. Preferably, the solvent is an alcohol. More preferably, the solvent is tert-butanol.

The preparation of cyclohexanone oxime using the titanium-silicalite molecular sieve of the present invention as the catalyst results in high conversion rate of cyclohexanone, high selectivity of cyclohexanone oxime and high usage efficiency of hydrogen peroxide.

DETAILED DESCRIPTION OF THE INVENTION

The following specific embodiments are provided to illustrate the disclosure of the present invention. These and other advantages and effects can be easily understood by those skilled in the art after reading the disclosure of this specification.

Comparative Example 1

A flask (500 ml) was nitrogen sealed under vacuum. 1.98 g of tetrabutyl titanate was added into the flask, and then cooled down to 5° C. Then, 30 g of tetraethyl silicate was dropped into the flask, and then stirred for 1 hour. 56 g (20 wt %) of tetrapropylammonium hydroxide solution was dropped into the flask, and then stirred for 1 hour. Then, 44.8 g of water was added, and stirred for 1 hour. After the temperature of the reaction system was back to the room temperature, the mixture was stirred for 1 hour. Then, the mixture was heated at 85° C. for 2 hours to remove alcohol, then added with 80 g of water and stirred for 1 hour, so as to form the mixture solution. The mixture solution was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain Comparative Example catalyst sample 1.

Embodiment 1

A flask (500 ml) was nitrogen sealed under vacuum. 3.24 g of titanium ethylhexoxide was added into the flask, and then cooled down to 5° C. Then, 30 g of tetraethyl silicate was dropped into the flask, and then stirred for 1 hour. 56 g (20 wt %) of tetrapropylammonium hydroxide isopropanol solution was dropped into the flask, and then stirred for 1 hour. Then, 44.8 g of water was added, and stirred for 1 hour. After the temperature of the reaction system was back to the room temperature, the mixture was stirred for 1 hour. Then, the mixture was heated at 85° C. for 2 hours to remove alcohol, and then the gel mixture was formed. Then, 80 g of water was added to form the mixture solution. The mixture solution was sealed in a can, and was heated at 180° C. for 120 hours. Then, the solid was separated from the liquid, and was cleaned with pure water to be neutral. The solid was dried at 100° C., and calcined at 550° C. for 8 hours, so as to obtain Embodiment catalyst sample 1.

Embodiments 2-4

These embodiments are similar to Embodiment 1 except that the titanium source was 2.84 g (75 wt %) of titanium di-isopropoxide bis(acetylacetonate)isopropanol solution, 5.26 g (67 wt %) of titanium di(2-ethylhexoxy)bis(2-ethyl-1,3-hexanediolate)n-butanol solution or 3.40 g (80 wt %) of titanium bis(tri-ethanolamine)di-isopropoxide isopropanol solution. Then, Embodiment catalyst samples 2-4 were obtained.

Embodiment 5

A flask (500 ml) was nitrogen sealed under vacuum. 3.24 g of titanium ethylhexoxide was added into the flask, and then cooled down to 5° C. Then, 30 g of tetraethyl silicate was dropped into the flask, and then stirred for 1 hour. 56 g (20 wt %) of tetrapropylammonium hydroxide isopropanol solution was dropped into the flask, and then stirred for 1 hour. Then, 44.8 g of water was added, and stirred for 1 hour. After the temperature of the reaction system was back to the room temperature, the mixture was stirred for 1 hour. Then, the mixture was heated at 85° C. for 2 hours to remove alcohol, and then the gel mixture was formed. 10.8 g of Ludox AS-40 was dispersed in 73.5 g of water to form colloidal silica solution, which was then mixed with the gel mixture and stirred for 1 hour to form the mixture solution. The mixture solution was sealed in a can, and was heated at 180° C. for 120 hours. Then, the solid was separated from the liquid, and was cleaned with pure water to be neutral. The solid was dried at 100° C., and calcined at 550° C. for 8 hours, so as to obtain Embodiment catalyst sample 5.

Embodiments 6-8

These embodiments are similar to Embodiment 5 except that the titanium source was 2.84 g (75 wt %) of titanium di-isopropoxide bis(acetylacetonate)isopropanol solution, 5.26 g (67 wt %) of titanium di(2-ethylhexoxy)bis(2-ethyl-1,3-hexanediolate)n-butanol solution or 3.40 g (80 wt %) of titanium bis(tri-ethanolamine)di-isopropoxide isopropanol solution. Then, Embodiment catalyst samples 6-8 were obtained.

Embodiment 9

A flask (500 ml) was nitrogen sealed under vacuum. 5.26 g (67 wt %) of titanium di(2-ethylhexoxy)bis(2-ethyl-1,3-hexanediolate) was added into the flask, and then cooled down to 5° C. Then, 30.9 g of polyethoxysiloxane ES-28 was dropped into the flask, and then stirred for 1 hour. 56 g (20 wt %) of tetrapropylammonium hydroxide isopropanol solution was dropped into the flask, and then stirred for 1 hour. Then, 44.8 g of water was added, and stirred for 1 hour. After the temperature of the reaction system was back to the room temperature, the mixture was stirred for 1 hour. Then, the mixture was heated at 85° C. for 2 hours to remove alcohol, and then the gel mixture was formed. 10.8 g of Ludox AS-40 was dispersed in 73.5 g of water to form colloidal silica solution, which was then mixed with the gel mixture and stirred for 1 hour to form the mixture solution. The mixture solution was sealed in a can, and was heated at 180° C. for 120 hours. Then, the solid was separated from the liquid, and was cleaned with pure water to be neutral. The solid was dried at 100° C., and calcined at 550° C. for 8 hours, so as to obtain Embodiment catalyst sample 9.

Embodiment 10

This embodiment was similar to Embodiment 9 except that the titanium source was 3.40 g (80 wt %) of titanium bis(tri-ethanolamine)di-isopropoxide isopropanol solution. Then, Embodiment catalyst sample 10 was obtained.

Embodiment 11

The titanium-silicalite molecular sieves prepared from Comparative Example 1 and Embodiments 1-10 were respectively used as the catalyst for the preparation of cyclohexanone oxime, and the activity of the titanium-silicalite molecular sieves was determined.

0.55 g of the catalyst was placed in a flask, and added with 5 g of cyclohexanone and 5.43 g (28 wt %) of ammonia. The reaction system was equipped with a condensation tube and a stirring device. The temperature of the reaction system was heated to 60° C., and then 5.43 g of 35 wt % hydrogen peroxide solution was gradually added to perform the preparation of cyclohexanone oxime. The introduction of hydrogen peroxide was performed for 5 hours, and then the reaction was performed for 1 more hour. Then, the reaction solution was analyzed by gas chromatography and a titrator. The results were shown in Table 1.

TABLE 1

|  | $X_K$ | $S_{OX}$ | $X_H$ | $S_H$ |
| --- | --- | --- | --- | --- |
| Comparative Example 1 | 99.60 | 98.16 | 99.04 | 89.33 |
| Embodiment 1 | 99.44 | 99.02 | 99.20 | 90.19 |
| Embodiment 2 | 99.68 | 99.42 | 99.58 | 90.90 |
| Embodiment 3 | 99.30 | 99.20 | 99.17 | 90.78 |
| Embodiment 4 | 99.60 | 99.43 | 99.50 | 90.91 |
| Embodiment 5 | 99.63 | 99.61 | 99.28 | 90.44 |
| Embodiment 6 | 99.84 | 99.93 | 98.42 | 92.54 |
| Embodiment 7 | 99.78 | 99.72 | 99.26 | 91.50 |
| Embodiment 8 | 99.76 | 99.40 | 99.01 | 90.98 |
| Embodiment 9 | 99.59 | 98.23 | 99.22 | 89.60 |
| Embodiment 10 | 99.94 | 98.17 | 99.37 | 89.76 |

$X_K$: conversion rate of cyclohexanone = moles of consumed cyclohexanone/initial moles of cyclohexanone × 100%
$S_{OX}$: selectivity of cyclohexanone oxime = moles of produced cyclohexanone oxime/moles of consumed cyclohexanone × 100%
$X_H$: conversion rate of hydrogen peroxide = moles of consumed hydrogen peroxide/initial moles of hydrogen peroxide × 100%
$S_H$: selectivity of hydrogen peroxide = moles of produced cyclohexanone oxime/moles of consumed hydrogen peroxide × 100%

Accordingly, the present invention provides a method for preparing a titanium-silicalite molecular sieve with high catalyst activity. The present invention further provides a method for preparing cyclohexanone oxime using the titanium-silicalite molecular sieve of the present invention as the catalyst, resulting in high selectivity, high conversion rate and high usage of hydrogen peroxide.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A method for preparing a titanium-silicalite molecular sieve, comprising the steps of:

preparing a mixture of a titanium source, a silicon source and a template agent, wherein the titanium source has a structure of formula (I)

$$\begin{array}{c} R_3 \\ | \\ O \\ | \\ R_4-O-Ti-O-R_2 \\ | \\ R_1 \end{array} \quad (I)$$

wherein $R_1$, $R_2$, $R_3$ and $R_4$ are independently $C_1$-$C_{10}$alkyl, $C_1$-$C_{10}$alkoxy, $C_2$-$C_{10}$hydroxyalkyl, $$-C(CH3)=CH-\overset{O}{\overset{\|}{C}}-CH_3 \text{ or } -(CH_2)_2-N\begin{array}{c} R_5-OH, \\ \diagup \\ \diagdown \\ R_6-OH \end{array}$$

in which $R_5$ and $R_6$ are independently $C_1$-$C_3$alkyl, and at least two of $R_1$, $R_2$, $R_3$ and $R_4$ have a carbon number more than 4;
heating the mixture to form a gel mixture;
mixing the gel mixture with water;
heating the gel mixture mixed with the water in a water bath; and
calcining the gel mixture mixed with the water.

2. The method of claim 1, wherein $R_1$ is $C_6$-$C_{10}$alkoxy, and $R_2$, $R_3$ and $R_4$ are independently $C_6$-$C_{10}$alkyl.

3. The method of claim 1, wherein $R_1$ is $C_6$-$C_{10}$alkyl, and $R_2$ and $R_3$ are independently $C_2$-$C_{10}$hydroxyalkyl, and $R_4$ is $C_6$-$C_{10}$alkyl.

4. The method of claim 1, wherein $R_1$ is $C_1$-$C_4$alkoxy, $R_2$ and $R_3$ are independently $$-C(CH3)=CH-\overset{O}{\overset{\|}{C}}-CH_3 \text{ or } -(CH_2)_2-N\begin{array}{c} R_5-OH, \\ \diagup \\ \diagdown \\ R_6-OH \end{array}$$

and $R_4$ is $C_1$-$C_4$alkyl.

5. The method of claim 4, wherein $R_1$ is $C_1$-$C_4$alkoxy, $R_2$ and $R_3$ are $$-C(CH3)=CH-\overset{O}{\overset{\|}{C}}-CH_3,$$

and $R_4$ is $C_1$-$C_4$alkyl.

6. The method of claim 4, wherein $R_1$ is $C_1$-$C_3$alkoxy, $R_2$ and $R_3$ are $$-(CH_2)_2-N\begin{array}{c} R_5-OH, \\ \diagup \\ \diagdown \\ R_6-OH \end{array}$$

and $R_4$ is $C_1$-$C_3$alkyl.

7. The method of claim 1, wherein the silicon source is tetraalkyl silicate, polyethoxysiloxane or a mixture thereof.

8. The method of claim 1, wherein the template agent is tetrapropylammonium hydroxide.

9. The method of claim 1, wherein the template agent includes at least one solvent, and the solvent is selected from alcohol solvents.

10. The method of claim 9, wherein the template agent includes one or more alcohol solvents selected from the group consisting of methanol, ethanol, isopropanol, n-butanol and tert-butanol, and a concentration of the template agent is 5 to 50 wt %.

11. The method of claim 9, wherein the gel mixture mixed with the water is heated to remove the solvent.

12. The method of claim 1, wherein the water includes silicon dioxide, and the silicon dioxide is 0.1 to 50 wt % of the water.

13. The method of claim 12, wherein a weight ratio of the water to the gel mixture ranges from 0.001:1 to 0.5:1.

14. The method of claim 1, wherein a molar ratio of the titanium source to the silicon source ranges from 0.005:1 to 0.06:1; and a molar ratio of the template agent to the silicon source ranges from 0.1:1 to 0.5:1.

15. A method for preparing cyclohexanone oxime, comprising the step of performing a reaction of cyclohexanone, ammonia and hydrogen peroxide in the presence of a titanium-silicalite molecular sieve of claim 1 and a solvent.

16. The method of claim 15, wherein a molar ratio of the ammonia to the cyclohexanone ranges from 1.2:1 to 2:1.

17. The method of claim 15, wherein a molar ratio of the hydrogen peroxide to the cyclohexanone ranges from 0.7:1 to 2.0:1.

18. The method of claim 15, wherein the solvent is a polar solvent, and the polar solvent is one or more selected from the group consisting of an alcohol, a ketone and water.

19. The method of claim 15, wherein the solvent is tert-butanol.

20. The method of claim 15, wherein an amount of the titanium-silicalite molecular sieve is 0.1 to 10 wt % of a total weight of the cyclohexanone, the ammonia and the hydrogen peroxide.

* * * * *